United States Patent [19]

Matsushita et al.

[11] 4,341,634

[45] Jul. 27, 1982

[54] ANALYTICAL METHOD OF HYDROCARBON COMPOUNDS

[75] Inventors: Susumu Matsushita; Yoshimitsu Tada, both of Shin-nanyo; Tetsuo Ikushige, Yamaguchi, all of Japan

[73] Assignee: Toyo Soda Manufacturing Co., Ltd., Shin-nanyo, Japan

[21] Appl. No.: 212,613

[22] Filed: Dec. 3, 1980

[30] Foreign Application Priority Data

Dec. 21, 1979 [JP] Japan .................................. 54-165604

[51] Int. Cl.$^3$ ............................................. B01D 15/08
[52] U.S. Cl. .................................. 210/656; 23/230 M
[58] Field of Search ............ 210/656, 659, 635, 198.2; 55/67, 386; 23/230 M; 208/310 R

[56] References Cited

PUBLICATIONS

Chromatographic and Allied Methods by Mikes; John Wiley & Sons, New York, pp. 156–161 and 179–183 (1979).
Chromatography in Petroleum Analysis by Altgelt, published by Marcel Dekker, Inc., New York, N.Y., pp. 244–247.
Suatoni et al., "Rapid Hydrocarbon Group–Type Analysis by High Performance Liquid Chromatography", Journal of Chromatographic Science, v. 13, (1975), pp. 361–365.
Suatoni et al., "Hydrocarbon Group Types in Gasoline-Range Materials by High Performance Liquid Chromatography", Journal of Chromatographic Science, vol. 13 (1975), pp. 367–371.
McKay et al., "High Performance Liquid Chromatographic Separation of Olefin, Saturate, and Aromatic Hydrocarbons in High-Boiling Distillates and Residues of Shale Oil," Anal. Chem. (1980), v. 52, pp. 1618–1621.

*Primary Examiner*—John Adee
*Attorney, Agent, or Firm*—Oblon, Fisher, Spivak, McClelland & Maier

[57] ABSTRACT

A high speed liquid chromatography to separate hydrocarbon compounds contained in a solution into three components, namely, saturates, unsaturates and aromatics, an analytical method of hydrocarbons which comprises
(a) using an organic chlorine-containing type solvent or a mixed solvent of an organic chlorine-containing type solvent and a hydrocarbon type solvent as an eluent;
(b) connecting the first column into which a silica type packing material is packed and the second column into which a silver-containing silica type packing material is packed in series; and
(c) introducing the eluate from the second column to a detector to detect it quantitatively.

5 Claims, 1 Drawing Figure

ANALYTICAL METHOD OF HYDROCARBON COMPOUNDS

BACKGROUND OF THE INVENTION

1. Field of the Invention

The present invention relates to an analytical method to quickly and automatically separate many kinds of hydrocarbon compounds contained in a solution into three types, namely, saturates, unsaturates and aromatics and analyze them.

2. Description of the Prior Art

The requirement to separate many kinds of hydrocarbon compounds contained in a solution into three groups of saturates, unsaturates and aromatics and analyze them is an immutable one. Recently this requirement becomes increasingly remarkable because the revision of the standards for fuel oils and the like are clamored.

Heretofore, a method, so-called fluorescent indicator adsoption method described in JIS K 2536 or ASTM D 1319 has been carried out for such a requirement; however, from the current practical viewpoint, there are various problems in these methods such as complicated operation and long time required for analysis.

A high speed liquid chromatograhy which has been remarkably developed in recent years is one of the methods to solve these problems. As these analytical methods using high speed chromatography, there has been known the instance wherein n-hexane or a fluorine-containing compound is used; however, this method has some disadvantages such as low solubility and high cost of hydrocarbon compound and complexity of device such as adoption of back flash mode. Further, a problem still remains in the performance of quantitative analysis since a differential refractometer is used in detection part.

SUMMARY OF THE INVENTION

It is an object of the present invention to overcome the above-mentioned disadvantages and to provide an analitical method of hydrocarbon compounds wherein the saturates, unsaturates and aromatics in a solution consisting of many kinds of hydrocarbon compounds can be easily and quickly analyzed with high reproducibility and accuracy was found. The foregoing and other objects have been attained by providing a chromatographical analytical method of hydrocarbon compounds which comprises in a high speed liquid chromatograph which separates hydrocarbon compounds contained in a solution into three components of saturates, unsaturates and aromatics, using an organic chlorine-containing type solvent or a mixed solvent of an organic chlorine-containing type solvent and a hydrocarbon type solvent as an eluent, connecting the first column into which a silica type packing material is packed and the second column into which a silver-containing silica type packing material is packed in series, separating said hydrocarbon compounds into (saturates+unsaturates) and aromatics in the first column, elutriating the saturates, unsaturates and aromatics from the second column in this order without substantially damaging the separation of the components elutriated from the first column, introducing the same into a detector and detecting the same quantitatively.

BRIEF DESCRIPTION OF THE DRAWINGS

In FIG. 1, P shows the elution location of the saturates, O shows that of the unsaturates and A shows that of the aromatics.

DETAILED DESCRIPTION OF THE PREFERRED EMBODIMENTS

Figure 1:
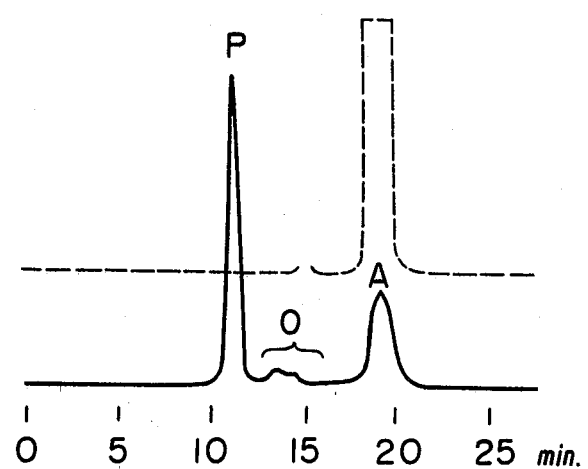
FIG. 1 shows the chromatogram of a gasoline on the market obtained according to the present invention. The solid line is a chromatogram obtained with an infrared detector (wave length: $3.4\mu$) and the broken line is one obtained with an ultraviolet detector (wave length: 270 nm).

The saturates, unsaturates and aromatics mentioned in the present invention are the classifications generally and commonly used in chemical fields and the compounds having similar chemical properties are collected into a group. For instance, the saturates designate naphthenic and paraffinic hydrocarbons; the unsaturates designate monoolefinic and cycloolefinic hydrocarbons and the aromatics designate alkylbenzene, naphthenic aromatic hydrocarbons, dicyclic, tricyclic and tetracyclic aromatic hydrocarbons and the like.

As suitable examples of samples to which the present invention is applied, there can be illustrated petroleum products such as gasoline, jet fuel, kerosene and heavy oil.

The amount of the sample to be fed in the present invention can be selected as the case may be; however, usually 0.5–200 $\mu$l is sufficient for the purpose.

A packing material which has a performance to sufficiently separate (saturates+unsaturates) from aromatics is necessary for the first column used in the present invention.

The performance to sufficiently separate mentioned herein means that (saturates+unsaturates) are distinctly separated from aromatics and the base lines of said both are distinctly separated in the result shown by the recorder.

For this purpose, at first, as a packing material for the first column, a wholly porous silica type packing material having a pore distribution in a range of 80–100 Å, a particle size in a range of 4–40 $\mu$m and specific surface area in a range of 380–570 $m^2/g$ such as a crushed type gel obtained by crushing a gel prepared by treating a solution of sodium silicate with a mineral acid such as sulfuric acid to cause gelation or a spherical gel obtained by diffusing sodium silicate in an organic solvent and agitating the solution to cause gelation is used.

In the second column, it is aimed to further adsorb only the unsaturates selectively from (saturates+unsaturates) and aromatics separated in the first column and elutriate the same in the order of saturates, unsaturates and aromatics. The particular packing material for this purpose is prepared, for instance, by physically and chemically treating silver on a silica type packing material as the carrier. This is a silver-containing silica type packing material obtained by treating a silver salt, for example, an organic or an inorganic acid salt, a halogenide or an oxide such as silver nitrite, silver nitrate, silver carbonate, silver acetate, silver lactate, silver chloride or silver oxide on a silica type packing material by physical and/or chemical means such as impregnation, heating or chemical reaction.

The content of silver in the silica gel carrier is preferably in a range of 0.05–20 wt.%; when it is less than 0.05 wt.%, the performance to adsorb silver is too low; however, a high content exceeding 20 wt.% is undesirable since the unsaturates are retained so firmly that the elution location thereof may superpose on that of the aromatics or elutriated more later.

As the detector used in the present invention, there is illustrated an infrared detector having a high sensitivity to hydrocarbon compounds and a high performance for quantitative measurement. An infrared analysis has been already widely used as an quantitative analytical means; however, the infrared detector for the present invention is used as a detector for high speed liquid chromatograph; accordingly, a particular infrared detector having a small size, a light weight, a cell volume in a range of 5-50 μl and a performance of high sensitivity is required.

As the measuring wave lengths of the infrared detector used in the present invention, those of 3.4μ, 3.5μ, 6.8μ and 7.2μ are selected for the saturates; those of 3.3μ, 3.4μ, 3.5μ, 6.1μ, 7.2μ and 10μ are selected for the unsaturates and those of 3.3μ, 3.4μ, 3.5μ, 6.2μ, 6.8μ and 7.2μ are selected for the aromatics. Among these measuring wave lengths, a wave length of 3.4μ is particularly preferable because it has a high sensitivity to the saturates, unsaturates and aromatics and enables one to measure them quantitatively. Also a detector having a characteristic to detect each component can be connected to the infrared detector in series. For instance, an analysis with high accuracy can be achieved by using an infrared detector and an ultraviolet detector since the saturates and unsaturates are detected with high sensitivities by the infrared detector and the aromatics are detected with high sensitivities by the ultraviolet detector.

In the chromatographic analysis of the present invention, the selection of eluent is also an important matter. As matters to be attended to, there are illustrated following items:

(1) relationship between detector and solvent
(2) viscosity of solvent
(3) boiling point of solvent
(4) water content in solvent
(5) solubility of sample In the case of (1), for instance, a solvent having no absorption in ultraviolet region is desirable when an ultraviolet detector is used and one having little absorption in infrared region is desirable when an infrared detector is used.

In the case of (2), if the solvent has a high viscosity, the elution movement becomes slow causing disadvantages such as decrease of column efficiency and increase of pressure loss; consequently, a solvent having a viscosity in a range of 0.4-1 poise at 20° C. is desirable.

In the case of (3), when the boiling point is low, it causes the generation of bubbles in detector; however, high boiling point is also undesirable for fractionation; consequently, it is desirable that the boiling point is in a range of 40°-200° C. at atmospheric pressure.

In the case of (4), since silica type packing materials are packed in both of the first and the second columns used in the present invention, it is undesirable to use a hygroscopic solvent which causes the variation in water content of silica type packing materials; consequently, a solvent having a solubility of water in a range of 0.0001-0.2 g/100 g water is desirable.

In the case of (5), a solvent in which the sample can be dissolved is desirable. If the solubility is low, the sample is adsorbed resulting in a long time required for analysis.

As another matter to be attended to, it is necessary to avoid solvents which tend to be easily decomposed or those which have risks such as fire or explosion. Consequently, as the solvent used as an eluent in the present invention, an organic chlorine-containing type solvent or a mixed solvent of an organic chlorine-containing type solvent and a hydrocarbon type solvent (hereinbelow called mixed solvent) is illustrated.

As an organic chlorine-containing type solvent, methylene chloride, chloroform, carbon tetrachloride, ethylene chloride, 1,1-dichloroethane, 1,1,1-trichloroethane, 1,1,2-trichloroethane, 1,1,1,2-tetrachloroethane, hexachloroethane, etc. can be illustrated; however, it is particularly desirable to use carbon tetrachloride.

The mixed solvent is prepared by mixing a hydrocarbon type solvent with an organic chlorine-containing type solvent; the mixing ratio is not higher than 1.0 vol.% preferably 0.5 vol.%. A high ratio exceeding 1.0 vol.% is undesirable since the measuring wave length of infrared ray is disturbed.

As a hydrocarbon type solvent, benzene, n-hexane, n-heptane, n-octane and n-nonane are illustrated; however, it is particularly desirable to use benzene.

As stated above, the present invention relates to an analytical method which consists of, in a high speed liquid chromatograph, connecting the first column consisting of a porous silica type packing material and the second column consisting of a silver-containing silica type packing material prepared by the treatment of silver in series, using an organic chlorine-containing type solvent or a mixed solvent as an eluent, injecting a solution consisting of various hydrocarbon compounds, separating them into three groups of the saturates, unsaturates and aromatics to elutriate them, introducing the hydrocarbon compounds into a detector to detect them highly sensitively and quantitatively, separating various hydrocarbon compounds in a solution into the saturates, unsaturates and aromatics and quantitatively analyzing them quickly and conveniently with high reproducibility and accuracy.

The detailed description of the present invention will be given hereinbelow with Examples and Comparative examples.

EXAMPLE 1

A liquid chromatograph on the market, type "HLC-803A" (trade name of a high speed liquid chromatograph manufactured by Toyo Soda Industries Co., Ltd.) consisting of a pump, an injection inlet and an ultraviolet and visible wave length variable detector was used to which an infrared detector for a high speed liquid chromatograph, type "MIRAN-1A" (trade name) manufactured by Toyo Soda/Wilkus was connected in series. As the first column was used a column made of stainless steel having an inside diameter of 7.5 mm and a length of 50 cm into which spherical wholly porous silica gel (TSK-GEL LS-320 (trade name) manufactured by Toyo Soda Industries Co., Ltd.) having a particle size of 5≠1μ and a specific area of 380 m²/g prepared by diffusing a solution of sodium silicate in an organic solvent and agitating the mixture to cause gelation was packed. As the second column was used a column made of stainless steel having an inside diameter of 4 mm and a length of 4 cm into which silver-silica type packing material prepared by making spherical, wholly porous silica gel (TSK-GEL LS-310 (trade name) manufactured by Toyo Soda Industries Co., Ltd.) having a particle size of 10≠2μ and a specific area of 400 m²/g prepared by diffusing a solution of sodium silicate in an organic solvent and agitating the mixture to cause gelation adsorb silver nitrate by 2 wt.% was packed. This was connected to the first column in series; carbon tetrachloride as the eluent was allowed to flow at a rate of 1.3 ml/min at room temperature and 2 μl of a regular gasoline on the market was injected into the column to make it pass through the columns; the measurement was conducted at an infrared ray having a wave length of 3.4μ. As a result, a chromatogram shown by the solid line in FIG. 1 was obtained.

The value of area was obtained from the electric signal same as that drawn in the chromatogram using a data processor (Data Processor "CP8-III" (trade name) manufactured by Toyo Soda Industries Co., Ltd.) and then volume percentage was calculated. Thus, the processed data were obtained and the results of analysis of the gasoline on the market could be obtained as follows: saturates(P): 53.0 vol.%, unsaturates(O): 1.4 vol.% and aromatics(A): 45.6 vol.%.

As obviously seen from the solid line chromatogram in FIG. 1, the time required for the separation of one sample was as short as 20 minutes and the separation was carried out with high reproducibility. Further, only the aromatics were measured at a wave length of 270 nm using the ultraviolet detector; as a result, a broken line chromatogram shown in FIG. 1 was obtained.

Hereafter, a mixed solvent prepared by mixing 0.5 vol.% of benzene with carbon tetrachloride was used as the eluent; the measurement was carried out in the same manner as that mentioned above and similar results were obtained.

EXAMPLE 2

The analysis of a kerosene on the market was carried out in accordance with the same conditions as those in Example 1 except packing wholly porous silica gel used in Example 1 into the first column made of stainless steel having an inside diameter of 7.5 mm and a length of 30 cm and packing silver-silica type packing material prepared by making wholly porous silica gel used in Example 1 retain 5 wt.% of silver nitrate thereon into the second column made of stainless steel having an inside diameter of 4 mm and a length of 4 cm. There were obtained the results as follows: saturates: 81.2 vol.%, unsaturates: 0.3 vol.% and aromatics: 18.5 vol.%.

EXAMPLE 3

The analysis of a naphtha was carried out in accordance with the same conditions as those in Example 1 except using carbon tetrachloride as the eluent and measuring with infrared rays having the wave lengths of 3.5μ, 6.25μ and 10μ. There were obtained the results as follows: saturates: 75.2 vol.%, unsaturates: 0.2 vol.% and aromatics: 24.6 vol.%.

Comparative example 1

The analysis was carried out in accordance with the same elution conditions as those in Example 1 except using n-hexane as the eluent and using a differential refractometer for the detector. As a result, the separation of the saturates and unsaturates was confirmed; however, it took more than 1 hour for the elution of the aromatics and the quantitative analysis was substantially impossible.

Comparative example 2

The analysis was carried out in accordance with the same elution conditions as those in Example 1 except eliminating the second column used in Example 1. As a result, the separation of the saturates and unsaturates was not complete and an accurate quantitative analysis was impossible. Also when the analysis was carried out in accordance with the same elution conditions as those in Example 1 except eliminating the first column to use the second column only, the unsaturates superposed on the aromatics and the analysis was impossible.

Comparative example 3

The separation of hydrocarbon compounds such as gasoline, kerosene and naphtha was carried out in accordance with the same elution conditions as those in Example 1 except using a differential refractometer as the detector. The separation of the saturates, unsaturates and aromatics was satisfactory; however, there were much differences in refraction indexes depending upon the kind of hydrocarbon compound and the quantitative analysis was substantially impossible.

We claim:

1. A quantitative analytical method for separating a sample of hydrocarbon compounds contained in a solution into three components, namely, saturates, unsaturates and aromatics present in the sample, by means of high speed liquid chromatography employing two columns connected in series, the first column being one into which a porous silica type packing material is packed and the second column being one into which a silver-containing silica type packing material is packed, which comprises the steps of:
    (a) introducing the liquid sample into the first column,
    (b) thereafter introducing into the first column as the eluent liquid an organic chlorine-containing type solvent or a mixed solvent composed of an organic chlorine-containing type solvent and up to 1 vol % of a hydrocarbon type solvent;
    (c) allowing the introduced liquids to pass through both columns in series; and
    (d) introducing the eluate from the second column into a detector to detect it quantitatively for saturates, unsaturates and aromatics, the three components having been chromatographicaly separated by steps (a), (b) and (c).

2. The method according to claim 1 wherein the organic chlorine-containing type solvent is methylene chloride, chloroform, carbon tetrachloride, ethylene chloride, 1,1-dichloroethane, 1,1,1-trichloroethane, 1,1,2-trichloroethane, 1,1,1,2-tetrachloroethane or hexachloroethane, and the hydrocarbon type solvent in the mixed solvent is benzene, n-hexane, n-heptane, n-octane or n-nonane.

3. The method according to claim 2 wherein the eluent is carbon tetrachloride.

4. The method according to claim 2 wherein the eluent is a mixed solvent composed of carbon tetrachloride and benzene.

5. The method according to claims 3 or 4 wherein the porous silica type packing material in the first column is a crushed silica gel and in which in the second column the content of silver in the silica type packing material is in the range of 0.05–20 wt %.

* * * * *